(12) United States Patent
Hossainy et al.

(10) Patent No.: US 9,364,498 B2
(45) Date of Patent: *Jun. 14, 2016

(54) HEPARIN PRODRUGS AND DRUG DELIVERY STENTS FORMED THEREFROM

(75) Inventors: Syed Faiyaz Ahmed Hossainy, Fremont, CA (US); Ni Ding, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 704 days.

This patent is subject to a terminal disclaimer.

(21) Appl. No.: 12/489,219

(22) Filed: Jun. 22, 2009

(65) Prior Publication Data

US 2009/0258054 A1 Oct. 15, 2009

Related U.S. Application Data

(63) Continuation of application No. 10/871,658, filed on Jun. 18, 2004, now Pat. No. 7,563,780.

(51) Int. Cl.
| | |
|---|---|
| *A61K 31/727* | (2006.01) |
| *A61F 2/00* | (2006.01) |
| *A61P 7/02* | (2006.01) |
| *A61K 47/48* | (2006.01) |
| *A61L 31/10* | (2006.01) |
| *A61L 31/16* | (2006.01) |
| *C08B 37/00* | (2006.01) |
| *C09D 105/10* | (2006.01) |

(52) U.S. Cl.
CPC ........... *A61K 31/727* (2013.01); *A61K 47/4823* (2013.01); *A61L 31/10* (2013.01); *A61L 31/16* (2013.01); *C08B 37/0075* (2013.01); *C09D 105/10* (2013.01); *A61L 2300/236* (2013.01); *A61L 2300/606* (2013.01); *A61L 2300/80* (2013.01)

(58) Field of Classification Search
None
See application file for complete search history.

(56) References Cited

U.S. PATENT DOCUMENTS

| | | | |
|---|---|---|---|
| 2,072,303 A | 3/1937 | Herrmann et al. | |
| 2,386,454 A | 10/1945 | Frosch et al. | |
| 3,773,737 A | 11/1973 | Goodman et al. | |
| 3,849,514 A | 11/1974 | Gray, Jr. et al. | |
| 4,226,243 A | 10/1980 | Shalaby et al. | |
| 4,329,383 A | 5/1982 | Joh | |
| 4,331,697 A | 5/1982 | Kudo et al. | |
| 4,343,931 A | 8/1982 | Barrows | |
| 4,440,926 A * | 4/1984 | Mardiguian | 536/21 |
| 4,529,792 A | 7/1985 | Barrows | |
| 4,611,051 A | 9/1986 | Hayes et al. | |
| 4,654,327 A | 3/1987 | Teng | |
| 4,656,242 A | 4/1987 | Swan et al. | |
| 4,733,665 A | 3/1988 | Palmaz | |
| 4,800,882 A | 1/1989 | Gianturco | |
| 4,871,357 A * | 10/1989 | Hsu et al. | 604/266 |
| 4,882,168 A | 11/1989 | Casey et al. | |
| 4,886,062 A | 12/1989 | Wiktor | |
| 4,931,287 A | 6/1990 | Bae et al. | |
| 4,941,870 A | 7/1990 | Okada et al. | |
| 4,977,901 A | 12/1990 | Ofstead | |
| 5,019,096 A | 5/1991 | Fox, Jr. et al. | |
| 5,047,020 A | 9/1991 | Hsu | |
| 5,069,899 A | 12/1991 | Whitbourne et al. | |
| 5,100,992 A | 3/1992 | Cohn et al. | |
| 5,112,457 A | 5/1992 | Marchant | |
| 5,133,742 A | 7/1992 | Pinchuk | |
| 5,163,952 A | 11/1992 | Froix | |
| 5,165,919 A | 11/1992 | Sasaki et al. | |
| 5,202,431 A | 4/1993 | Della Valle et al. | |
| 5,219,980 A | 6/1993 | Swidler | |
| 5,236,570 A | 8/1993 | Ma et al. | |
| 5,258,020 A | 11/1993 | Froix | |
| 5,270,046 A | 12/1993 | Sakamoto et al. | |
| 5,270,064 A | 12/1993 | Shultz | |
| 5,272,012 A | 12/1993 | Opolski | |
| 5,288,711 A | 2/1994 | Mitchell et al. | |
| 5,292,516 A | 3/1994 | Viegas et al. | |
| 5,298,260 A | 3/1994 | Viegas et al. | |
| 5,300,295 A | 4/1994 | Viegas et al. | |

(Continued)

FOREIGN PATENT DOCUMENTS

| | | |
|---|---|---|
| DE | 42 24 401 | 1/1994 |
| EP | 0 301 856 | 2/1989 |

(Continued)

OTHER PUBLICATIONS

Klement, Biomaterials, 2002.*

(Continued)

*Primary Examiner* — Susan Tran
*Assistant Examiner* — William Craigo
(74) *Attorney, Agent, or Firm* — Squire Patton Boggs (US) LLP

(57) ABSTRACT

A prodrug comprising a heparin and a drug is provided. The prodrug can be used to form a coating on a medical device. The prodrug can also be used with a polymeric material to form a coating on a medical device. The polymeric material can be a hydrophobic polymer, a hydrophilic polymer, a non-fouling polymer, or combinations thereof. The medical device can be implanted in a human being for the treatment of a disease such as atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, or combinations thereof.

9 Claims, 1 Drawing Sheet

(56) References Cited

U.S. PATENT DOCUMENTS

| | | | |
|---|---|---|---|
| 5,306,501 | A | 4/1994 | Viegas et al. |
| 5,306,786 | A | 4/1994 | Moens et al. |
| 5,328,471 | A | 7/1994 | Slepian |
| 5,330,768 | A | 7/1994 | Park et al. |
| 5,380,299 | A | 1/1995 | Fearnot et al. |
| 5,388,711 | A | 2/1995 | Hodges |
| 5,417,981 | A | 5/1995 | Endo et al. |
| 5,447,724 | A | 9/1995 | Helmus et al. |
| 5,453,171 | A | 9/1995 | Ma et al. |
| 5,455,040 | A | 10/1995 | Marchant |
| 5,462,990 | A | 10/1995 | Hubbell et al. |
| 5,464,650 | A | 11/1995 | Berg et al. |
| 5,485,496 | A | 1/1996 | Lee et al. |
| 5,516,881 | A | 5/1996 | Lee et al. |
| 5,569,463 | A | 10/1996 | Helmus et al. |
| 5,578,073 | A | 11/1996 | Haimovich et al. |
| 5,584,877 | A | 12/1996 | Miyake et al. |
| 5,605,696 | A | 2/1997 | Eury et al. |
| 5,607,467 | A | 3/1997 | Froix |
| 5,609,629 | A | 3/1997 | Fearnot et al. |
| 5,610,241 | A | 3/1997 | Lee et al. |
| 5,616,338 | A | 4/1997 | Fox, Jr. et al. |
| 5,624,411 | A | 4/1997 | Tuch |
| 5,628,730 | A | 5/1997 | Shapland et al. |
| 5,644,020 | A | 7/1997 | Timmermann et al. |
| 5,649,977 | A | 7/1997 | Campbell |
| 5,658,995 | A | 8/1997 | Kohn et al. |
| 5,667,767 | A | 9/1997 | Greff et al. |
| 5,670,558 | A | 9/1997 | Onishi et al. |
| 5,674,242 | A | 10/1997 | Phan et al. |
| 5,679,400 | A | 10/1997 | Tuch |
| 5,700,286 | A | 12/1997 | Tartaglia et al. |
| 5,702,754 | A | 12/1997 | Zhong |
| 5,711,958 | A | 1/1998 | Cohn et al. |
| 5,714,477 | A | 2/1998 | Einarsson |
| 5,716,981 | A | 2/1998 | Hunter et al. |
| 5,721,131 | A | 2/1998 | Rudolph et al. |
| 5,723,219 | A | 3/1998 | Kolluri et al. |
| 5,735,897 | A | 4/1998 | Buirge |
| 5,741,881 | A * | 4/1998 | Patnaik ................... 528/75 |
| 5,746,998 | A | 5/1998 | Torchilin et al. |
| 5,759,205 | A | 6/1998 | Valentini |
| 5,770,563 | A | 6/1998 | Roberts et al. |
| 5,776,184 | A | 7/1998 | Tuch |
| 5,783,657 | A | 7/1998 | Pavlin et al. |
| 5,788,979 | A | 8/1998 | Alt et al. |
| 5,800,392 | A | 9/1998 | Racchini |
| 5,820,917 | A | 10/1998 | Tuch |
| 5,824,048 | A | 10/1998 | Tuch |
| 5,824,049 | A | 10/1998 | Ragheb et al. |
| 5,830,178 | A | 11/1998 | Jones et al. |
| 5,837,008 | A | 11/1998 | Berg et al. |
| 5,837,313 | A | 11/1998 | Ding et al. |
| 5,849,859 | A | 12/1998 | Acemoglu |
| 5,851,508 | A | 12/1998 | Greff et al. |
| 5,854,376 | A | 12/1998 | Higashi |
| 5,855,618 | A | 1/1999 | Patnaik et al. |
| 5,858,746 | A | 1/1999 | Hubbell et al. |
| 5,865,814 | A | 2/1999 | Tuch |
| 5,869,127 | A | 2/1999 | Zhong |
| 5,873,904 | A | 2/1999 | Ragheb et al. |
| 5,876,433 | A | 3/1999 | Lunn |
| 5,877,224 | A | 3/1999 | Brocchini et al. |
| 5,879,713 | A | 3/1999 | Roth et al. |
| 5,902,875 | A | 5/1999 | Roby et al. |
| 5,905,168 | A | 5/1999 | Dos Santos et al. |
| 5,910,564 | A | 6/1999 | Gruning et al. |
| 5,914,387 | A | 6/1999 | Roby et al. |
| 5,919,893 | A | 7/1999 | Roby et al. |
| 5,925,720 | A | 7/1999 | Kataoka et al. |
| 5,932,299 | A | 8/1999 | Katoot |
| 5,955,509 | A | 9/1999 | Webber et al. |
| 5,958,385 | A | 9/1999 | Tondeur et al. |
| 5,962,138 | A | 10/1999 | Kolluri et al. |
| 5,971,954 | A | 10/1999 | Conway et al. |
| 5,980,928 | A | 11/1999 | Terry |
| 5,980,972 | A | 11/1999 | Ding |
| 5,997,517 | A | 12/1999 | Whitbourne |
| 6,010,530 | A | 1/2000 | Goicoechea |
| 6,011,125 | A | 1/2000 | Lohmeijer et al. |
| 6,015,541 | A | 1/2000 | Greff et al. |
| 6,033,582 | A | 3/2000 | Lee et al. |
| 6,034,204 | A | 3/2000 | Mohr et al. |
| 6,042,875 | A | 3/2000 | Ding et al. |
| 6,051,576 | A | 4/2000 | Ashton et al. |
| 6,051,648 | A | 4/2000 | Rhee et al. |
| 6,054,553 | A | 4/2000 | Groth et al. |
| 6,056,993 | A | 5/2000 | Leidner et al. |
| 6,060,451 | A | 5/2000 | DiMaio et al. |
| 6,060,518 | A | 5/2000 | Kabanov et al. |
| 6,080,488 | A | 6/2000 | Hostettler et al. |
| 6,080,767 | A | 6/2000 | Klein et al. |
| 6,096,070 | A | 8/2000 | Ragheb et al. |
| 6,099,562 | A | 8/2000 | Ding et al. |
| 6,110,188 | A | 8/2000 | Narciso, Jr. |
| 6,110,483 | A | 8/2000 | Whitbourne et al. |
| 6,113,629 | A | 9/2000 | Ken |
| 6,120,491 | A | 9/2000 | Kohn et al. |
| 6,120,536 | A | 9/2000 | Ding et al. |
| 6,120,788 | A | 9/2000 | Barrows |
| 6,120,904 | A | 9/2000 | Hostettler et al. |
| 6,121,027 | A | 9/2000 | Clapper et al. |
| 6,129,761 | A | 10/2000 | Hubbell |
| 6,136,333 | A | 10/2000 | Cohn et al. |
| 6,143,354 | A | 11/2000 | Koulik et al. |
| 6,153,252 | A | 11/2000 | Hossainy et al. |
| 6,159,978 | A | 12/2000 | Myers et al. |
| 6,165,212 | A | 12/2000 | Dereume et al. |
| 6,172,167 | B1 | 1/2001 | Stapert et al. |
| 6,177,523 | B1 | 1/2001 | Reich et al. |
| 6,180,632 | B1 | 1/2001 | Myers et al. |
| 6,203,551 | B1 | 3/2001 | Wu |
| 6,211,249 | B1 | 4/2001 | Cohn et al. |
| 6,214,901 | B1 | 4/2001 | Chudzik et al. |
| 6,231,600 | B1 | 5/2001 | Zhong |
| 6,240,616 | B1 | 6/2001 | Yan |
| 6,245,753 | B1 * | 6/2001 | Byun et al. ................... 514/56 |
| 6,245,760 | B1 | 6/2001 | He et al. |
| 6,248,129 | B1 | 6/2001 | Froix |
| 6,251,136 | B1 | 6/2001 | Guruwaiya et al. |
| 6,254,632 | B1 | 7/2001 | Wu et al. |
| 6,258,121 | B1 | 7/2001 | Yang et al. |
| 6,258,371 | B1 | 7/2001 | Koulik et al. |
| 6,262,034 | B1 | 7/2001 | Mathiowitz et al. |
| 6,270,788 | B1 | 8/2001 | Koulik et al. |
| 6,277,449 | B1 | 8/2001 | Kolluri et al. |
| 6,283,947 | B1 | 9/2001 | Mirzaee |
| 6,283,949 | B1 | 9/2001 | Roorda |
| 6,284,305 | B1 | 9/2001 | Ding et al. |
| 6,287,628 | B1 | 9/2001 | Hossainy et al. |
| 6,299,604 | B1 | 10/2001 | Ragheb et al. |
| 6,306,176 | B1 | 10/2001 | Whitbourne |
| 6,331,313 | B1 | 12/2001 | Wong et al. |
| 6,335,029 | B1 | 1/2002 | Kamath et al. |
| 6,344,035 | B1 | 2/2002 | Chudzik et al. |
| 6,346,110 | B2 | 2/2002 | Wu |
| 6,358,556 | B1 | 3/2002 | Ding et al. |
| 6,379,381 | B1 | 4/2002 | Hossainy et al. |
| 6,387,379 | B1 | 5/2002 | Goldberg et al. |
| 6,395,326 | B1 | 5/2002 | Castro et al. |
| 6,419,692 | B1 | 7/2002 | Yang et al. |
| 6,451,373 | B1 | 9/2002 | Hossainy et al. |
| 6,482,834 | B2 | 11/2002 | Spada et al. |
| 6,494,862 | B1 | 12/2002 | Ray et al. |
| 6,503,538 | B1 | 1/2003 | Chu et al. |
| 6,503,556 | B2 | 1/2003 | Harish et al. |
| 6,503,954 | B1 | 1/2003 | Bhat et al. |
| 6,506,437 | B1 | 1/2003 | Harish et al. |
| 6,517,858 | B1 | 2/2003 | Le Moel et al. |
| 6,524,347 | B1 | 2/2003 | Myers et al. |
| 6,527,801 | B1 | 3/2003 | Dutta |
| 6,527,863 | B1 | 3/2003 | Pacetti et al. |
| 6,528,526 | B1 | 3/2003 | Myers et al. |
| 6,530,950 | B1 | 3/2003 | Alvarado et al. |

(56) References Cited

U.S. PATENT DOCUMENTS

| | | | |
|---|---|---|---|
| 6,530,951 B1 | 3/2003 | Bates et al. | |
| 6,534,481 B1 | 3/2003 | Driguez et al. | |
| 6,540,776 B2 | 4/2003 | Sanders Millare et al. | |
| 6,541,116 B2 | 4/2003 | Michal et al. | |
| 6,541,488 B1 * | 4/2003 | Bernat et al. | 514/327 |
| 6,544,223 B1 | 4/2003 | Kokish | |
| 6,544,543 B1 | 4/2003 | Mandrusov et al. | |
| 6,544,582 B1 | 4/2003 | Yoe | |
| 6,555,157 B1 | 4/2003 | Hossainy | |
| 6,558,733 B1 | 5/2003 | Hossainy et al. | |
| 6,562,781 B1 | 5/2003 | Berry et al. | |
| 6,565,659 B1 | 5/2003 | Pacetti et al. | |
| 6,572,644 B1 | 6/2003 | Moein | |
| 6,585,755 B2 | 7/2003 | Jackson et al. | |
| 6,585,765 B1 | 7/2003 | Hossainy et al. | |
| 6,585,926 B1 | 7/2003 | Mirzaee | |
| 6,589,943 B2 | 7/2003 | Byun et al. | |
| 6,605,154 B1 | 8/2003 | Villareal | |
| 6,616,765 B1 | 9/2003 | Hossainy et al. | |
| 6,623,448 B2 | 9/2003 | Slater | |
| 6,625,486 B2 | 9/2003 | Lundkvist et al. | |
| 6,630,580 B2 | 10/2003 | Tsang et al. | |
| 6,645,135 B1 | 11/2003 | Bhat | |
| 6,645,195 B1 | 11/2003 | Bhat et al. | |
| 6,656,216 B1 | 12/2003 | Hossainy et al. | |
| 6,656,506 B1 | 12/2003 | Wu et al. | |
| 6,660,034 B1 | 12/2003 | Mandrusov et al. | |
| 6,663,662 B2 | 12/2003 | Pacetti et al. | |
| 6,663,880 B1 | 12/2003 | Roorda et al. | |
| 6,666,880 B1 | 12/2003 | Chiu et al. | |
| 6,673,154 B1 | 1/2004 | Pacetti et al. | |
| 6,673,385 B1 | 1/2004 | Ding et al. | |
| 6,689,099 B2 | 2/2004 | Mirzaee | |
| 6,695,920 B1 | 2/2004 | Pacetti et al. | |
| 6,706,013 B1 | 3/2004 | Bhat et al. | |
| 6,709,514 B1 | 3/2004 | Hossainy | |
| 6,712,845 B2 | 3/2004 | Hossainy | |
| 6,713,119 B2 | 3/2004 | Hossainy et al. | |
| 6,716,444 B1 | 4/2004 | Castro et al. | |
| 6,723,120 B2 | 4/2004 | Yan | |
| 6,733,768 B2 | 5/2004 | Hossainy et al. | |
| 6,740,040 B1 | 5/2004 | Mandrusov et al. | |
| 6,743,462 B1 | 6/2004 | Pacetti | |
| 6,749,626 B1 | 6/2004 | Bhat et al. | |
| 6,753,071 B1 | 6/2004 | Pacetti et al. | |
| 6,758,859 B1 | 7/2004 | Dang et al. | |
| 6,759,054 B2 | 7/2004 | Chen et al. | |
| 6,764,505 B1 | 7/2004 | Hossainy et al. | |
| 6,896,965 B1 | 5/2005 | Hossainy | |
| 6,953,784 B2 | 10/2005 | Thompson et al. | |
| 6,969,705 B2 | 11/2005 | Pecquet et al. | |
| 7,129,224 B1 | 10/2006 | Byun et al. | |
| 7,160,867 B2 | 1/2007 | Abel et al. | |
| 7,226,611 B2 | 6/2007 | Yura et al. | |
| 7,393,840 B2 | 7/2008 | Rosemberg et al. | |
| 7,396,541 B2 | 7/2008 | Hossainy et al. | |
| 7,438,925 B2 | 10/2008 | Hsu | |
| 2001/0007083 A1 * | 7/2001 | Roorda | 623/1.15 |
| 2001/0014717 A1 | 8/2001 | Hossainy et al. | |
| 2001/0018469 A1 | 8/2001 | Chen et al. | |
| 2001/0020011 A1 | 9/2001 | Mathiowitz et al. | |
| 2001/0029351 A1 | 10/2001 | Falotico et al. | |
| 2001/0037145 A1 | 11/2001 | Guruwaiya et al. | |
| 2001/0051608 A1 | 12/2001 | Mathiowitz et al. | |
| 2002/0005206 A1 | 1/2002 | Falotico et al. | |
| 2002/0007213 A1 | 1/2002 | Falotico et al. | |
| 2002/0007214 A1 | 1/2002 | Falotico | |
| 2002/0007215 A1 | 1/2002 | Falotico et al. | |
| 2002/0009604 A1 | 1/2002 | Zamora et al. | |
| 2002/0009782 A1 | 1/2002 | Miron | |
| 2002/0013292 A1 | 1/2002 | Byun et al. | |
| 2002/0016625 A1 | 2/2002 | Falotico et al. | |
| 2002/0032414 A1 | 3/2002 | Ragheb et al. | |
| 2002/0032434 A1 | 3/2002 | Chudzik et al. | |
| 2002/0051730 A1 | 5/2002 | Bodnar et al. | |
| 2002/0055621 A1 | 5/2002 | Diaz et al. | |
| 2002/0071822 A1 | 6/2002 | Uhrich | |
| 2002/0077693 A1 | 6/2002 | Barclay et al. | |
| 2002/0082679 A1 | 6/2002 | Sirhan et al. | |
| 2002/0087123 A1 | 7/2002 | Hossainy et al. | |
| 2002/0091433 A1 | 7/2002 | Ding et al. | |
| 2002/0094440 A1 | 7/2002 | Llanos et al. | |
| 2002/0111590 A1 | 8/2002 | Davila et al. | |
| 2002/0120326 A1 | 8/2002 | Michal | |
| 2002/0123801 A1 | 9/2002 | Pacetti et al. | |
| 2002/0142039 A1 | 10/2002 | Claude | |
| 2002/0155212 A1 | 10/2002 | Hossainy | |
| 2002/0165608 A1 * | 11/2002 | Llanos et al. | 623/1.45 |
| 2002/0176849 A1 | 11/2002 | Slepian | |
| 2002/0183581 A1 | 12/2002 | Yoe et al. | |
| 2002/0188037 A1 | 12/2002 | Chudzik et al. | |
| 2002/0188277 A1 | 12/2002 | Roorda et al. | |
| 2003/0004141 A1 | 1/2003 | Brown | |
| 2003/0028243 A1 | 2/2003 | Bates et al. | |
| 2003/0028244 A1 | 2/2003 | Bates et al. | |
| 2003/0031780 A1 | 2/2003 | Chudzik et al. | |
| 2003/0032767 A1 | 2/2003 | Tada et al. | |
| 2003/0036794 A1 | 2/2003 | Ragheb et al. | |
| 2003/0039689 A1 * | 2/2003 | Chen et al. | 424/468 |
| 2003/0040712 A1 | 2/2003 | Ray et al. | |
| 2003/0040790 A1 | 2/2003 | Furst | |
| 2003/0059520 A1 | 3/2003 | Chen et al. | |
| 2003/0060877 A1 | 3/2003 | Falotico et al. | |
| 2003/0065377 A1 | 4/2003 | Davila et al. | |
| 2003/0072868 A1 | 4/2003 | Harish et al. | |
| 2003/0073961 A1 | 4/2003 | Happ | |
| 2003/0083646 A1 | 5/2003 | Sirhan et al. | |
| 2003/0083739 A1 | 5/2003 | Cafferata | |
| 2003/0097088 A1 | 5/2003 | Pacetti | |
| 2003/0097173 A1 | 5/2003 | Dutta | |
| 2003/0099684 A1 | 5/2003 | Domb | |
| 2003/0099712 A1 | 5/2003 | Jayaraman | |
| 2003/0105518 A1 | 6/2003 | Dutta | |
| 2003/0113439 A1 | 6/2003 | Pacetti et al. | |
| 2003/0124705 A1 * | 7/2003 | Berry et al. | 435/226 |
| 2003/0130206 A1 | 7/2003 | Koziak et al. | |
| 2003/0150380 A1 | 8/2003 | Yoe | |
| 2003/0157241 A1 | 8/2003 | Hossainy et al. | |
| 2003/0158517 A1 | 8/2003 | Kokish | |
| 2003/0161884 A1 | 8/2003 | Rosenberg et al. | |
| 2003/0190406 A1 | 10/2003 | Hossainy et al. | |
| 2003/0207020 A1 | 11/2003 | Villareal | |
| 2003/0211230 A1 | 11/2003 | Pacetti et al. | |
| 2003/0229390 A1 | 12/2003 | Ashton et al. | |
| 2003/0236221 A1 | 12/2003 | DeFerra et al. | |
| 2004/0018296 A1 | 1/2004 | Castro et al. | |
| 2004/0029952 A1 | 2/2004 | Chen et al. | |
| 2004/0037886 A1 | 2/2004 | Hsu | |
| 2004/0047978 A1 | 3/2004 | Hossainy et al. | |
| 2004/0047980 A1 | 3/2004 | Pacetti et al. | |
| 2004/0052858 A1 | 3/2004 | Wu et al. | |
| 2004/0052859 A1 | 3/2004 | Wu et al. | |
| 2004/0054104 A1 | 3/2004 | Pacetti | |
| 2004/0060508 A1 | 4/2004 | Pacetti et al. | |
| 2004/0062853 A1 | 4/2004 | Pacetti et al. | |
| 2004/0063805 A1 | 4/2004 | Pacetti et al. | |
| 2004/0071861 A1 | 4/2004 | Mandrusov et al. | |
| 2004/0072796 A1 | 4/2004 | Embury et al. | |
| 2004/0072922 A1 | 4/2004 | Hossainy et al. | |
| 2004/0073298 A1 | 4/2004 | Hossainy | |
| 2004/0077592 A1 | 4/2004 | Thompson et al. | |
| 2004/0086542 A1 | 5/2004 | Hossainy et al. | |
| 2004/0086550 A1 | 5/2004 | Roorda et al. | |
| 2004/0087543 A1 | 5/2004 | Shriver et al. | |
| 2004/0096504 A1 | 5/2004 | Michal | |
| 2004/0098117 A1 | 5/2004 | Hossainy et al. | |
| 2004/0141945 A1 | 7/2004 | Yura et al. | |
| 2005/0266038 A1 | 12/2005 | Glauser et al. | |

FOREIGN PATENT DOCUMENTS

| | | |
|---|---|---|
| EP | 0 396 429 | 11/1990 |
| EP | 0 514 406 | 11/1992 |
| EP | 0 604 022 | 6/1994 |

(56) References Cited

FOREIGN PATENT DOCUMENTS

| | | |
|---|---|---|
| EP | 0 623 354 | 11/1994 |
| EP | 0 665 023 | 8/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 023 879 | 8/2000 |
| EP | 1 192 957 | 4/2002 |
| EP | 1 273 314 | 1/2003 |
| JP | 2001-190687 | 7/2001 |
| RU | 790725 | 2/1983 |
| RU | 1016314 | 5/1983 |
| RU | 811750 | 9/1983 |
| RU | 1293518 | 2/1987 |
| SU | 872531 | 10/1981 |
| SU | 876663 | 10/1981 |
| SU | 905228 | 2/1982 |
| WO | WO 91/12846 | 9/1991 |
| WO | WO 94/09760 | 5/1994 |
| WO | WO 95/10989 | 4/1995 |
| WO | WO 95/24929 | 9/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/08463 | 3/1998 |
| WO | WO 98/17331 | 4/1998 |
| WO | WO 98/32398 | 7/1998 |
| WO | WO 98/36784 | 8/1998 |
| WO | WO 98/47948 | 10/1998 |
| WO | WO 99/01118 | 1/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/51027 | 7/2001 |
| WO | WO 01/74414 | 10/2001 |
| WO | WO 02/03890 | 1/2002 |
| WO | WO 02/26162 | 4/2002 |
| WO | WO 02/34311 | 5/2002 |
| WO | WO 02/056790 | 7/2002 |
| WO | WO 02/058753 | 8/2002 |
| WO | WO 02/102283 | 12/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/080147 | 10/2003 |
| WO | WO 03/082368 | 10/2003 |
| WO | WO 04/000383 | 12/2003 |
| WO | WO 2004/000383 A2 | 12/2003 |
| WO | WO 2004/009145 | 1/2004 |

OTHER PUBLICATIONS

Nathan, Macromolecules, 1992.*
Pharmpedia, Stability of Drugs, 2006.*
Hawley's Condensed Chemical Dictionary, 14$^{th}$ Ed., definition of "fragment", (2002).
Howell et al., PubMed Abstract of Pulm. Pharmacol. 6(4) pp. 237-239 (1993).
J. Invas. Cardiology 12 (3s) pp. 8B-15B (2000).
Jantzen and Robison, Modern Pharmaceutics, Third. Ed., Ed. by Banker and Rhodes, p. 596.
Liang et al., AAPS Pharm sci 2(1) article 7 (2000).
Liu et al., J. Biomed. Materials Res. 62(1), pp. 128-135 (2002).
Molinari et al., Proc. Natl. Acad. Sci. USA, vol. 74, No. 11, pp. 4886-4890 (1977).
Upchurch et al., PubMed Abstract of J. Cardiovasc. Pharmacol. Ther. Apr. 6(2), pp. 163-173 (2001).
Wikipedia, definition of "bioactive or biological activity", (2006).
Wikipedia, definition of "complex", (2007).
Wikipedia, definition of "derivative", (2007).
Wikipedia, definition of "metabolite", (2007).
Williams et al., Graefe's Arch. Clin. Exp. Ophthalmol. 234, pp. 496-503 (1996).
Wolf, Burger's Medicinal Chemistry and Drug Discovery, 5$^{th}$ Ed., vol. 1, pp. 975-977.
Hawley's Condensed Chemical Dictionary, 14$^{th}$ Ed., definition of "free radical" (2002).
Howell et al., PubMed abstract of Pulm. Pharmacol. 6(4): 237-9 (1993) 1 pg.
"Glycoprotein IIb/IIa Antagonist and Fibrinolytic Agents . . . ", J. of Invas. Cardiology, 12(3s): pp. 8B-15B, (2000) 3 pgs.
Jantzen and Robinson, Modern Pharmaceutics, Third edition, edited by Banker and Rhodes, pp. 596 (1996).
Liang et al., "Synthesis and Characterization of Positively Charged tPA as a Prodrug Using a Heparin/Protamine-Based Drug-Delivery System" AAPS Pharmsci: 2(1) article 7, 9 pgs. (2000).
Liu et al., Hyaluronate-heparin conjugate gels for the delivery of basic fibroblast growth factor (FGF-2), J. Biomed. Materials Research, 62(1), pp. 129-135 (2002).
Molinari et al., "Estradiol receptor of calf uterus: Interaction with heparin-agarose and purification", Proc. Natl. Acad. Sci. USA, vol. 74(11) pp. 4886-4890 (1977).
Upchurch, et al., "Heparin reacts with and Innactivates nitric oxide", PubMed Abstract of J. Cardiovasc. Pharmacol. Ther.6(2): pp. 163-173, 2 pgs. (2001).
Wikipedia, definition of "bioactive" or "biological activity" 1 pg. (2006).
Wikipedia, definition of "complex" 1 pg. (2007).
Wikipedia, definition of "derivative" 1 pg. (2007).
Wikipedia, definition of "metabolite" 8 pgs.(2007).
Williams et al., "Does the presence of heparin and dexamethasone in the vitrectomy infusate reduce reproliferation in proliferative vitreoretinopathy?", Graefe's Arch. Clin. Exp. Ophthalmol. 234: pp. 496-503 (1996).
Wolff, Burgers Medicinal Chemistry and Drug Discovery, 5th edition, vol. 1, pp. 975-977 (1995).
Porcari et al., "Recent advances in clinical trials of the direct and indirect selective Factor Xa inhibitors", Exp. Opin. Invest. Drugs 9(7), pp. 1595-1600 (2000).
Kim et al., "Absorption study of deoxycholic acid-heparin conjugate as a new form of oral anti-coagulant," J. Controlled Release 120, pp. 4-10 (2007).
Anonymous, *Cardiologists Draw—Up the Dream Stent*, Clinica 710:15 (Jun. 17, 1996), http://www.dialogweb.com/cgi/document?req=1061848202959, printed Aug. 25, 2003 (2 pages).
Anonymous, *Heparin-coated stents cut complications by 30%*, Clinica 732:17 (Nov. 18, 1996), http://www.dialogweb.com/cgi/document?req=1061847871753, printed Aug. 25, 2003 (2 pages).
Anonymous, *Rolling Therapeutic Agent Loading Device for Therapeutic Agent Delivery or Coated Stent* (Abstract 434009), Res. Disclos. pp. 974-975 (Jun. 2000).
Anonymous,*Stenting continues to dominate cardiology*, Clinica 720:22 (Sep. 2, 1996), http://www.dialogweb.com/cgi/document?req=1061848017752, printed Aug. 25, 2003 (2 pages).
Aoyagi et al., *Preparation of cross-linked aliphatic polyester and application to thermo-responsive material*, Journal of Controlled Release 32:87-96 (1994).

(56) References Cited

OTHER PUBLICATIONS

Barath et al., *Low Dose of Antitumor Agents Prevents Smooth Muscle Cell Proliferation After Endothelial Injury*, JACC 13(2): 252A (Abstract) (Feb. 1989).
Barbucci et al., *Coating of commercially available materials with a new heparinizable material*, J. Biomed. Mater. Res. 25:1259-1274 (Oct. 1991).
Chung et al., *Inner core segment design for drug delivery control of thermo-responsive polymeric micelles*, Journal of Controlled Release 65:93-103 (2000).
Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).
Dichek et al., *Seeding of Intravascular Stents with Genetically Engineered Endothelial Cells*, Circ. 80(5):1347-1353 (Nov. 1989).
Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).
Harper, *Drug Latentiation*, Prog. Drug Res. 4, pp. 221-294, (1962).
Helmus, *Overview of Biomedical Materials*, MRS Bulletin, pp. 33-38 (Sep. 1991).
Herdeg et al., *Antiproliferative Stent Coatings: Taxol and Related Compounds*, Semin. Intervent. Cardiol. 3:197-199 (1998).
Higuchi et al. eds., *Pro-drugs as Novel Drug Delivery Systems*, ACS Symposium ser. 14, pp. 1-115, (1975).
Huang et al., *Biodegradable Polymers Derived from Aminoacids*, Macromol. Symp. 144, 7-32 (1999).
Inoue et al., *An AB block copolymer of oligo(methyl methacrylate) and poly(acrylic acid) for micellar delivery of hydrophobic drugs*, Journal of Controlled Release 51:221-229 (1998).
Kataoka et al., *Block copolymer micelles as vehicles for drug delivery*, Journal of Controlled Release 24:119-132 (1993).
Katsarava et al., *Amino Acid-Based Bioanalogous Polymers. Synthesis and Study of Regular Poly(ester amide)s Based on Bis(α-amino acid)α,ω-Alkylene Diesters, and Aliphatic Dicarboxylic Acids*, Journal of Polymer Science, Part A: Polymer Chemistry, 37(4), 391-407 (1999).
Levy et al., *Strategies for Treating Arterial Restenosis Using Polymeric Controlled Release Implants*, Biotechnol. Bioact. Polym. [Proc. Am. Chem. Soc. Symp.], pp. 259-268 (1994).
Liu et al., *Drug release characteristics of unimolecular polymeric micelles*, Journal of Controlled Release 68:167-174 (2000).
Manfred E. Wolff, Burger's Medicinal Chemistry and Drug Discovery, 5th edition, vol. 1, pp. 975-977.
Marconi et al., *Covalent bonding of heparin to a vinyl copolymer for biomedical applications*, Biomaterials 18(12):885-890 (1997).
Matsumaru et al., *Embolic Materials for Endovascular Treatment of Cerebral Lesions*, J. Biomater. Sci. Polymer Edn 8(7):555-569 (1997).
Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).
Miyazawa et al., *Effects of Pemirolast and Tranilast on Intimal Thickening After Arterial Injury in the Rat*, J. Cardiovasc. Pharmacol., pp. 157-162 (1997).
Nordrehaug et al., *A novel biocompatible coating applied to coronary stents*, EPO Heart Journal 14, p. 321 (P1694), Abstr. Suppl. (1993).
Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).
Ozaki et al., *New Stent Technologies*, Progress in Cardiovascular Diseases, vol. XXXIX(2):129-140 (Sep./Oct. 1996).
Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).
Peng et al., *Role of polymers in improving the results of stenting in coronary arteries*, Biomaterials 17:685-694 (1996).
Roche Ed., *Design of Biopharmaceutical Properties through Prodrugs and Analogs*, book, (1977).
Saotome, et al., *Novel Enzymatically Degradable Polymers Comprising α-Amino Acid, 1,2-Ethanediol, and Adipic Acid*, Chemistry Letters, pp. 21-24, (1991).
Scully et al., *Effect of a heparan sulphate with high affinity for antithrombin upon inactivation of thrombin and coagulation Factor Xa*, Biochem J. 262, pp. 651-658, (1989).
Sehgal et al., *A Method for the High Efficiency of Water-Soluble Carbodiimide-Mediated Amidation*, Anal. Biochemistry 218, pp. 87-91, (1994).
Shigeno, *Prevention of Cerebrovascular Spasm by Bosentan, Novel Endothelin Receptor*, Chemical Abstract 125:212307 (1996).
Sincula et al., *Rationale for Design of Biologically Reversible Drug Derivatives: Prodrugs*, J. of Pharmaceutical Sciences, vol. 64, No. 2, pp. 181-210, Feb. 1975.
Staros et al., *Enhancement by N-Hydroxysulfosuccinimide of Water-Soluble Carbodimide-Mediated Coupling Reactions*, Anal. Biochemistry 156, pp. 220-222, (1986).
Stella et al., *Prodrugs do the have advantages in clinical Practice?* Drugs 29, pp. 455-473, (1985).
Tedder et al., *Basic Organic Chemistry* part 4, pp. 204-343, (1972).
van Beusekom et al., *Coronary stent coatings*, Coronary Artery Disease 5(7):590-596 (Jul. 1994).
Wilensky et al., *Methods and Devices for Local Drug Delivery in Coronary and Peripheral Arteries*, Trends Cardiovasc. Med. 3(5):163-170 (1993).
Yokoyama et al., *Characterization of physical entrapment and chemical conjugation of adriamycin in polymeric micelles and their design for in vivo delivery to a solid tumor*, Journal of Controlled Release 50:79-92 (1998).

* cited by examiner

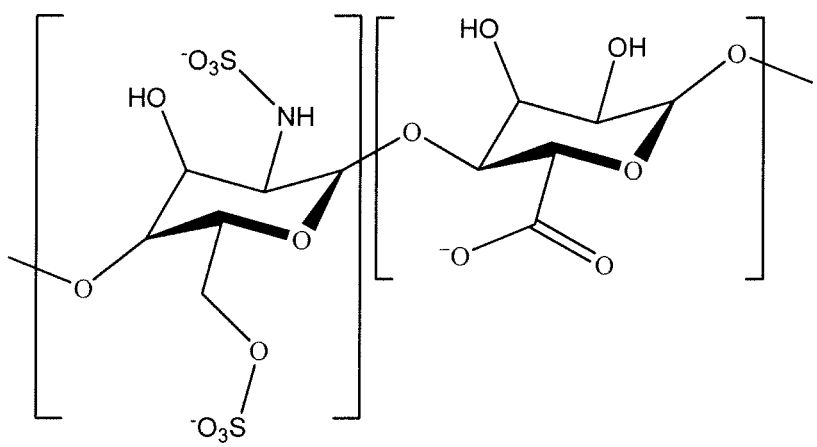

HEPARIN PRODRUGS AND DRUG DELIVERY STENTS FORMED THEREFROM

CROSS-REFERENCE TO RELATED APPLICATION

This application is a continuation application of U.S. application Ser. No. 10/871,658 filed on Jun. 18, 2004, the teaching of which is incorporated by reference herein in its entirety.

FIELD OF THE INVENTION

This invention generally relates to a prodrug formed of heparin and a drug and drug-delivery stents formed from a material having the prodrug.

DESCRIPTION OF THE BACKGROUND

Blood has a property of being coagulated by the action of various components in blood when it has come into contact with foreign matters. Hence, there is a need for a high anticoagulant property in component materials for medical articles or instruments used on the part coming into contact with blood, as exemplified by artificial hearts, artificial cardiac valves, artificial blood vessels, blood vessel catheters, cannulas, pump-oxygenators, blood vessel by-pass tubes, intraaortic balloon pumps, transfusion instruments and extracorporeal circulation circuits.

Heparin has been commonly used to impart to anticoagulant properties the medical devices, but a systemic use of heparin may undesirably lead to the formation of a large number of bleeding nests. Methods have been developed to minimize side effects associated with the use of heparin with limited success (see, for example, U.S. Pat. Nos. 5,270,064 and 6,630,580). Meanwhile, problems associated with systemic administration of a drug have led to the development of methods for local delivery of the drug. Administration of a pharmacologically active drug directly to a patient may lead to some undesirable consequences because many therapeutic drugs have undesirable properties that may become pharmacological, pharmaceutical, or pharmacokinetic barriers in clinical drug applications.

Therefore, in the art of drug-delivery implantable medical devices, there is a need for minimizing the side effects associated with the use of heparin and a drug.

The present invention addresses such problems by providing a coating composition and a coating formed thereof including a prodrug formed of heparin and a drug.

SUMMARY OF THE INVENTION

Provided herein is a prodrug having heparin and a drug in which the drug and heparin form a hydrolytically or enzymatically unstable linkage. The prodrug can be an ester type prodrug in which the drug molecule and the heparin molecule can form an ester bond formed of the carboxyl group in the heparin molecule and hydroxyl group in the drug or vice versa. The prodrug can be a Schiff-base-type prodrug in which a drug having an amine group and heparin functionalized to have an aldehyde group form a Schiff base or vice versa. The prodrug can also be an acetal- or hemi-acetal-type prodrug in which hydroxyl groups on a drug and heparin functionalized to have an aldehyde group or vice versa form an acetal or hemi-acetal.

The prodrug molecule can be used to form a coating on an implantable device. The prodrug can also be attached to a polymer via the heparin molecule to form a polymer bearing the prodrug defined herein, which can then be coated onto an implantable device. Alternatively, the prodrug can be grafted onto a polymeric coating on an implantable device.

In one embodiment, the prodrug can be used alone to form a coating on a medical device. In another embodiment, the prodrug can be used with a polymeric material to form a coating on a medical device. The polymeric material can be a hydrophobic polymer, a hydrophilic polymer, a non-fouling polymer, or combinations thereof. The medical device can be implanted in a human being for the treatment of a disease such as atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, or combinations thereof.

BRIEF DESCRIPTION OF THE DRAWING

FIG. 1 shows heparin's building blocks: glycosamine and iduronic acid.

DETAILED DESCRIPTION

Prodrugs Including Heparin

Many therapeutic drugs have undesirable properties that may become pharmacological, pharmaceutical, or pharmacokinetic barriers in clinical drug applications. Among the various approaches to minimize the undesirable drug properties while retaining the desirable therapeutic activity, a chemical approach using drug derivatization offers perhaps the highest flexibility and has been demonstrated as an important means of improving drug efficacy. The prodrug approach, a chemical approach using reversible derivatives, can be useful in the optimization of the clinical application of a drug. The prodrug approach gained attention as a technique for improving drug therapy in the early 1970s. Numerous prodrugs have been designed and developed since then to overcome pharmaceutical and pharmacokinetic barriers in clinical drug application, such as low oral drug absorption, lack of site specificity, chemical instability, toxicity, and poor patient acceptance (bad taste, odor, pain at injection site, etc.) (Stella V., Prodrugs: an overview and definition. In: Higuchi T., Stella V., eds. Prodrugs As Novel Drug Delivery Systems. ACS Symposium Series. Washington, D.C.: American Chemical Society; 1975:1-115).

As used herein, the term "prodrug" refers to an agent rendered less active by a chemical or biological moiety, which metabolizes into or undergoes in vivo hydrolysis to form a drug or an active ingredient thereof. The term "prodrug" can be used interchangeably with terms such as "proagent", "latentiated drugs," "bioreversible derivatives," and "congeners" (Harper N.J. Drug latentiation. Prog Drug Res. 1962; 4:221-294; Roche E B. Design of Biopharmaceutical Properties through Prodrugs and Analogs. Washington, D.C.: American Pharmaceutical Association; 1977; Sinkula A A, Yalkowsky S H. Rationale for design of biologically reversible drug derivatives: prodrugs. J Pharm Sci. 1975; 64:181-210). Usually, the use of the term implies a covalent link between a drug and a chemical moiety, though some authors also use it to characterize some forms of salts of the active drug molecule. Although there is no strict universal definition for a prodrug itself, and the definition may vary from author to author, generally prodrugs can be defined as pharmacologically inert chemical derivatives that can be converted in vivo, enzymatically or nonenzymatically, to the active drug molecules to exert a therapeutic effect (Sinkula A A, Yalkowsky S H. Rationale for design of biologically reversible drug derivatives: prodrugs. J Pharm Sci. 1975; 64:181-210; Stella V J, Charman W N, Naringrekar V H. Prodrugs. Do they have advantages in clinical practice? Drugs. 29:455-473 (1985)).

In one embodiment, the prodrug described herein includes a drug and heparin that form a linkage that can be enzymatically or hydrolytically cleaved under in vivo conditions. In some embodiments, the linkage can be an ester group, a Schiff base, or an acetal or hemi-acetal.

In another embodiment, the prodrug described herein can include a drug, a polymer and heparin. Heparin is conjugated or linked to the polymer by a physical or chemical linkage. The drug can link or be attached to the heparin or the polymer. In some embodiments, the linkage between heparin and the polymer can be, for example, ionic bonding, hydrogen bonding, or a chemical bonding such as an ester group, a Schiff base, or an acetal or hemi-acetal. The linkage between the drug and the polymer can be, for example, an ester group, a Schiff base, or an acetal or hemi-acetal, and the linkage between the drug and heparin can be, for example, an ester group, a Schiff base, or an acetal or hemi-acetal.

Heparin

The term "heparin" refers to a heparin molecule, a heparin fragment such as pentasaccharide, a heparin derivative or a heparin complex. Heparin derivatives can be any functional or structural variation of heparin. Representative variations include alkali metal or alkaline-earth metal salts of heparin, such as sodium heparin (e.g., hepsal or pularin), potassium heparin (e.g., clarin), lithium heparin, calcium heparin (e.g., calciparine), magnesium heparin (e.g., cutheparine), low molecular weight heparin (e.g., ardeparin sodium) with a molecular weight of from about 4,000 to about 5,000 Daltons and high affinity heparin (see, e.g., Scully, et al., Biochem. J. 262:651-658 (1989)). Other examples include heparin sulfate, heparinoids, heparin based compounds and heparin having a hydrophobic counter-ion such as tridodecylmethylammonium and benzalkonium.

Heparin contains both carboxyl groups and hydroxyl groups (FIG. 1). Carboxyl groups can form an ester linkage by reacting with hydroxyl reactive groups on a drug (see Scheme 1, below). Alternatively, the hydroxyl groups on heparin can also form an ester linkage by reacting with carboxyl groups on a drug (see Scheme 2, below).

In some other embodiments, the prodrug described herein can be formed of a functionalized heparin and a drug molecule. For example, Heparin-CHO can react with an amine group on a drug or vice versa to form a Schiff-base-type prodrug (see Scheme 3, below). Heparin-CHO can also react with hydroxyl groups on a drug or vice versa to form acetal or hemi-acetal type prodrugs (see Scheme 4, below).

Modification of Heparin

Heparin is a highly negatively charged molecule very soluble in water. It has some solubility in formamide, but is practically insoluble in other organic solvents. This lack of solubility in organic solvents limits its use in certain applications. The conventional method of improving the solubility of heparin in organic solvents can be achieved by complexing heparin with a positive charged organic moiety such as a quaternary ammonium salt, e.g. tridodecylmethylammoniumchloride and benzalkonium chloride. Some exemplary, useful hydrophobic quaternary ammonium compounds and methods of forming complexes of these compounds with heparin are described in U.S. Pat. Nos. 4,654,327, 4,871,357 and 5,047,020.

Heparin contains many reactive groups such as carboxyl, amine, and hydroxyl groups in its molecular structure. Partially oxidized heparin contains terminal aldehyde groups. Prior to or subsequent to forming the prodrug described above, in some embodiments, heparin can be physically or chemically (e.g. covalently) attached to hydrophilic and hydrophobic polymers by chemical reactions between the functional groups on heparin and the polymer. Heparin can also be copolymerized with other monomer(s) to form a polymer containing heparin. In some other embodiments, attachment of heparin can be accomplished by chemically (e.g. covalently) or physically coupling heparin onto a polymer-coated surface. Physical coupling includes, for example, ionic interaction or hydrogen bonding.

As used herein, the term "hydrophobic" refers to an attribute of a material that defines the degree of water affinity of the molecules of the material. Hydrophobicity and hydrophilicity are relative terms. Generally, hydrophobicity and hydrophilicity of a polymer can be gauged using the Hildebrand solubility parameter δ. The term "Hildebrand solubility parameter" refers to a parameter indicating the cohesive energy density of a substance. The δ parameter is determined as follows:

$$\delta = (\Delta E/V)^{1/2}$$

where δ is the solubility parameter, $(cal/cm^3)^{1/2}$;
ΔE is the energy of vaporization, cal/mole; and
V is the molar volume, $cm^3$/mole.

If a blend of hydrophobic and hydrophilic polymer(s) is used, whichever polymer in the blend has a lower δ value compared to the δ value of the other polymer in the blend is designated as a hydrophobic polymer, and the polymer with a higher δ value is designated as a hydrophilic polymer. If more than two polymers are used in the blend, then each can be ranked in order of its δ value. In some embodiments, the defining boundary between hydrophobic and hydrophilic can be set at 10.5, $(cal/cm^3)^{1/2}$.

Any biocompatible polymer can be used to modify the hydrophilicity of heparin. Representative hydrophobic polymers include, but are not limited to, poly(ester amide), polystyrene-polyisobutylene-polystyrene block copolymer (SIS), polystyrene, polyisobutylene, polycaprolactone (PCL), poly (L-lactide), poly(D,L-lactide), poly(lactides), polylactic acid (PLA), poly(lactide-co-glycolide), poly(glycolide), polyalkylene, polyfluoroalkylene, polyhydroxyalkanoate, poly(3-hydroxybutyrate), poly(4-hydroxybutyrate), poly(3-hydroxyvalerate), poly(3-hydroxybutyrate-co-3-hydroxyvalerate), poly(3-hydroxyhexanoate), poly(4-hyroxyhexanoate), mid-chain polyhydroxyalkanoate, poly (trimethylene carbonate), poly(ortho ester), polyphosphazenes, poly(phosphoester), poly(tyrosine derived arylates), poly(tyrosine derived carbonates), polydimethyloxanone (PDMS), polyvinylidene fluoride (PVDF), polyhexafluoropropylene (HFP), polydimethylsiloxane, poly (vinylidene fluoride-co-hexafluoropropylene) (PVDF-HFP), poly(vinylidene fluoride-co-chlorotrifluoroethylene) (PVDF-CTFE), poly(methacrylates) such as poly(butyl methacrylate) (PBMA) or poly(methyl methacrylate) (PMMA), poly(vinyl acetate), poly(ethylene-co-vinyl acetate), poly(ethylene-co-vinyl alcohol), poly(ester urethanes), poly(ether-urethanes), poly(carbonate-urethanes), poly(silicone-urethanes), poly(urea-urethanes) or a combination thereof. Methods of derivatizing heparin with hydrophobic materials or polymers are described in, for example, U.S.

Pat. Nos. 4,331,697; 5,069,899; 5,236,570; 5,270,046; 5,453,171; 5,741,881; 5,770,563; 5,855,618; 6,589,943 and 6,630,580.

Any hydrophobic counter ion can be used to modify the hydrophilicity of heparin. For example, hydrophobic quaternary ammonium compounds have been commonly used to form complexes with heparin that are soluble in organic solvents. Some exemplary useful hydrophobic quaternary ammonium compounds and methods of forming complexes of these compounds with heparin are described in U.S. Pat. Nos. 4,654,327, 4,871,357 and 5,047,020.

In some other embodiments, a hydrophilic polymer and/or a non-fouling polymer can be used to modify the hydrophilicity of heparin. Non-fouling or anti-fouling is defined as preventing, delaying or reducing the amount of formation of protein build-up caused by the body's reaction to foreign material. Representative hydrophilic polymers include, but are not limited to, polymers and co-polymers of PEG acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), hydroxyl bearing monomers such as HEMA, hydroxypropyl methacrylate (HPMA), hydroxypropylmethacrylamide, and 3-trimethylsilylpropyl methacrylate (TMSPMA), poly(ethylene glycol) (PEG), poly(propylene glycol), SIS-PEG, polystyrene-PEG, polyisobutylene-PEG, PCL-PEG, PLA-PEG, PMMA-PEG, PDMS-PEG, PVDF-PEG, PLURONIC™ surfactants (polypropylene oxide-co-polyethylene glycol), poly(tetramethylene glycol), poly(L-lysine-ethylene glycol) (PLL-g-PEG), poly(L-g-lysine-hyaluronic acid) (PLL-g-HA), poly(L-lysine-g-phosphoryl choline) (PLL-g-PC), poly(L-lysine-g-vinylpyrrolidone) (PLL-g-PVP), poly(ethylimine-g-ethylene glycol) (PEI-g-PEG), poly(ethylimine-g-hyaluronic acid) (PEI-g-HA), poly (ethylimine-g-phosphoryl choline) (PEI-g-PC), and poly (ethylimine-g-vinylpyrrolidone) (PEI-g-PVP), PLL-co-HA, PLL-co-PC, PLL-co-PVP, PEI-co-PEG, PEI-co-HA, PEI-co-PC, and PEI-co-PVP, hydroxy functional poly(vinyl pyrrolidone), polyalkylene oxide, dextran, dextrin, sodium hyaluronate, hyaluronic acid, elastin, chitosan, acrylic sulfate, acrylic sulfonate, acrylic sulfamate, methacrylic sulfate, methacrylic sulfonate, methacrylic sulfamate and combination thereof. The non-fouling polymer can be, for example, poly(ethylene glycol), poly(alkylene oxide), hydroxyethylmethacrylate (HEMA) polymer and copolymers, poly(n-propylmethacrylamide), sulfonated polystyrene, hyaluronic acid, poly(vinyl alcohol), poly(N-vinyl-2-pyrrolidone), sulfonated dextran, phosphoryl choline, choline, or combinations thereof.

The heparin can be readily attached to a polymer or polymeric surface by forming a Schiff base between an amino group and an aldehyde group that heparin and the polymer may have, by forming an amide group between an amine group on a polymer and the carboxyl group on heparin via NHS(N-hydroxysuccinimide) activation (see, e.g., Staros, et al., Anal. Biochem. 156:220-222 (1986)), EDC (1-ethyl-3-(3-dimethylaminopropyl) carbodiimide hydrochloride) activation (see, e.g., J. M. Tedder, A. Nechvatal, A. W. Murray, et al. Amino-acids and proteins. In: *Basic organic chemistry*. London: John Wiley & Sons, Chapter 6, pp. 305-342 (1972); D. Sehgal, I. K. Vijay, Anal. Biochem. 218:87 (1994)) or aziridine chemistry. Some representative methods of attaching heparin to a polymer or polymeric surface are described in U.S. application Ser. No. 10/857,141, filed on May 27, 2004, the teachings of which are incorporated herein by reference.

In a further embodiment, heparin can be derivatized with an unsaturated group such as acrylate, e.g., methacrylate, or vinyl alcohol using the chemistry described above. The heparin functionalized with an unsaturated group can be used in a free radical polymerization to graft or crosslink to a substrate or another formulation component such as a polymer.

Drugs

The drug can be any agent which is biologically active and capable of forming an ester bond with the carboxyl group or hydroxyl group of the heparin molecule or capable of forming a Schiff base or acetal or hemi-acetal with heparin functionalized to have an aldehyde group. In the alternative, the drug can have an aldehyde so as to react with the amino group of heparin-$NH_2$ to form a Schiff base prodrug or an aldehyde or keto group so as to react with the hydroxyl group or groups on heparin to acetal or hemi-acetal prodrug. Most drugs have one of hydroxyl, carboxyl, amino, keto or aldehyde groups and thus can form the prodrugs described herein.

The drug can be, for example, a therapeutic, prophylactic, or diagnostic agent. As used herein, the drug includes a bioactive moiety, derivative, or metabolite of the drug.

Examples of suitable therapeutic and prophylactic agents capable of forming the prodrugs described herein include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Other examples of drugs include antibodies, receptor ligands, and enzymes, adhesion peptides, oligosaccharides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy, In one embodiment, the drug can be a drug for inhibiting the activity of vascular smooth muscle cells. More specifically, the drug can be aimed at inhibiting abnormal or inappropriate migration and/or proliferation of smooth muscle cells for the inhibition of restenosis. The drug can also include any substance capable of exerting a therapeutic or prophylactic effect in the practice of the present invention. For example, the drug can be a prohealing drug that imparts a benign neointimal response characterized by controlled proliferation of smooth muscle cells and controlled deposition of extracellular matrix with complete luminal coverage by phenotypically functional (similar to uninjured, healthy intima) and morphologically normal (similar to uninjured, healthy intima) endothelial cells. The drug can also fall under the genus of antineoplastic, cytostatic or anti-proliferative, anti-inflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S. A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist, antibody, recombinant hirudin, and thrombin inhibitors such as Angiomax ä(Biogen, Inc., Cambridge, Mass.). Examples of cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.), actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. Other drugs include calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium.

Other therapeutic substances or agents which may be appropriate include alpha-interferon, genetically engineered epithelial cells, antibodies such as CD-34 antibody, abciximab (REOPRO), and progenitor cell capturing antibody, prohealing drugs that promotes controlled proliferation of muscle cells with a normal and physiologically benign composition and synthesis products, enzymes, anti-inflammatory agents, antivirals, anticancer drugs, anticoagulant agents, free radical scavengers, estradiol, steroidal anti-inflammatory agents, non-steroidal anti-inflammatory, antibiotics, nitric oxide donors, super oxide dismutases, super oxide dismutases mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, 40-O-tetrazole-rapamycin, ABT-578, clobetasol, cytostatic agents, aspirin, and a combination thereof.

The foregoing substances are listed by way of example and are not meant to be limiting. Other active agents which are currently available or that may be developed in the future are equally applicable.

The dosage or concentration of the drug required to produce a favorable therapeutic effect should be less than the level at which the drug produces toxic effects and greater than the level at which non-therapeutic results are obtained. The dosage or concentration of the drug can depend upon factors such as the particular circumstances of the patient, the nature of the trauma, the nature of the therapy desired, the time over which the ingredient administered resides at the vascular site, and, if other active agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Method of Forming a Prodrug

The carboxylic acid group of the heparin molecule can form an ester bond with a drug molecule via an established procedure in the art of organic synthesis (see, for example, Larock, Comprehensive Organic Transformations: A Guide to Functional Group Preparations, John Wiley & Sons, Inc., Copyright 1999). Generally, the prodrug described herein can be prepared according to Scheme 1, as described below.

Scheme 1

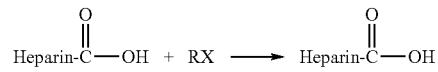

In Scheme 1, R represents a drug molecule or a derivative thereof. Heparin represents a heparin molecule or a moiety or derivative thereof. X represents a leaving group attached to the drug molecule. For example, X can be OH, a halo group, mesylate or tosyl group, and any other groups capable of leaving the drug molecule in forming the drug/heparin ester bond.

The prodrug can be an ester formed between a carboxyl group of heparin and a hydroxyl group of the drug. The drug can be paclitaxel, docetaxel, estradiol, tacrolimus, dexamethasone, rapamycin, 40-O-(2-hydroxy)ethyl-rapamycin (everolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (ABT-578), or clobetasol for example.

Tacrolimus has the following structural formula:

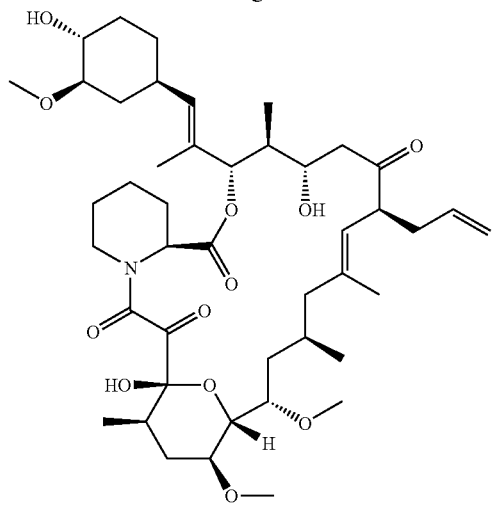

Rapamycin has the following structural formula:

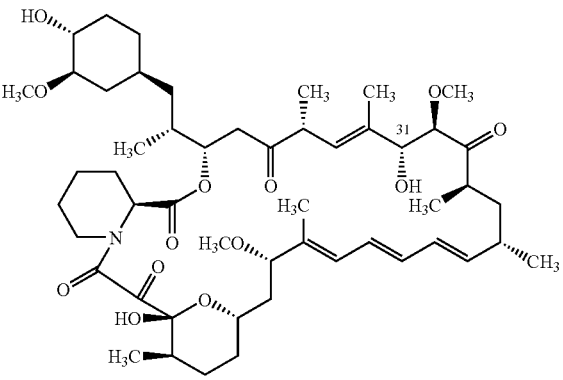 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC(=O)[C@H](C)/C=C(\C)[C@@H](O)[C@@H](OC)C(=O)[C@H](C)C[C@H](C)/C=C/C=C/C=C/1C]

40-O-(2-hydroxy)ethyl-rapamycin (Everolimus) has the following structural formula:

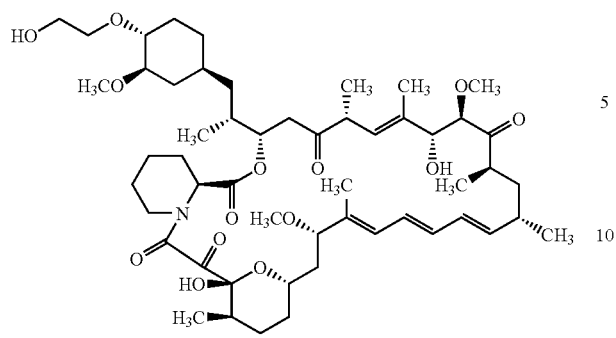
40-O-(3-hydroxy) propyl-rapamycin has the following structural formula:
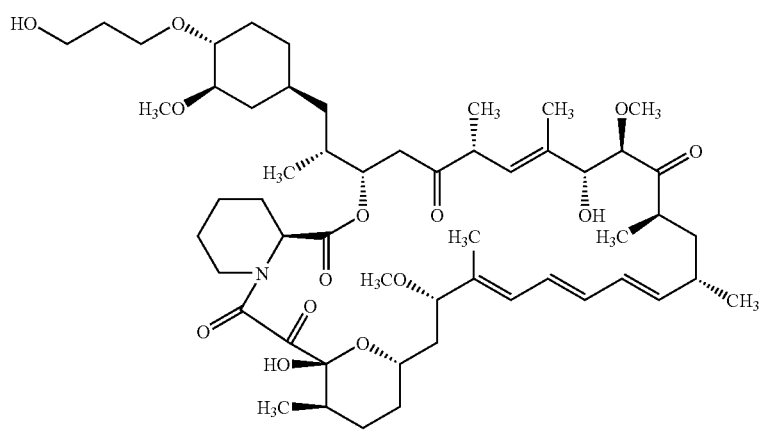 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OCCCO)[C@H](OC)C2)CC(=O)[C@H](C)/C=C(\C)[C@@H](O)[C@@H](OC)C(=O)[C@H](C)C[C@H](C)/C=C/C=C/C=C/1C]
40-O-[2-(2-hydroxy) ethoxy]ethyl-rapamycin has the following structural formula:
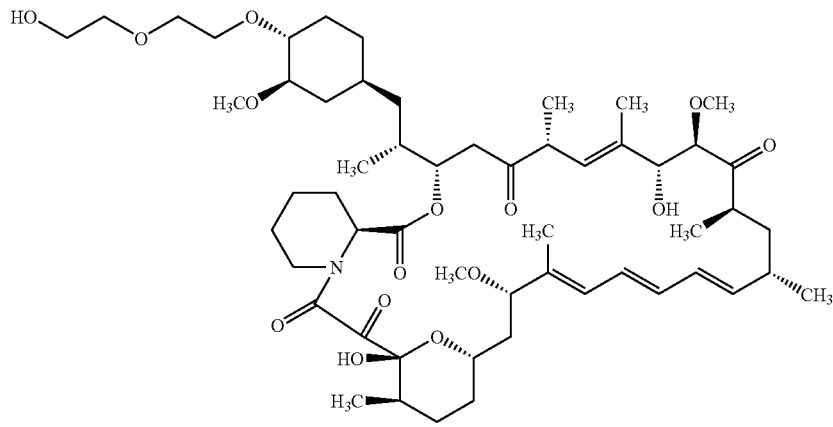 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OCCOCCO)[C@H](OC)C2)CC(=O)[C@H](C)/C=C(\C)[C@@H](O)[C@@H](OC)C(=O)[C@H](C)C[C@H](C)/C=C/C=C/C=C/1C]

40-O-tetrazole-rapamycin has the following structural formula:

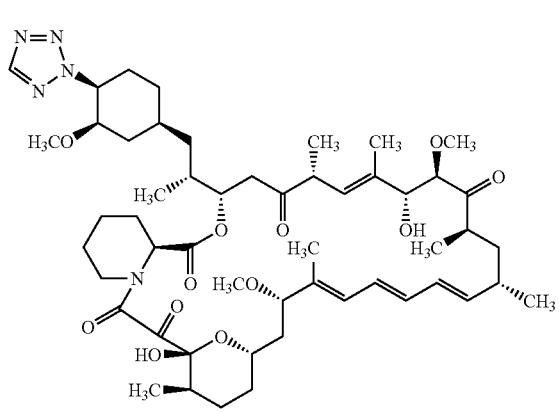 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@H](n3ncnn3)[C@H](OC)C2)CC(=O)[C@H](C)/C=C(\C)[C@@H](O)[C@@H](OC)C(=O)[C@H](C)C[C@H](C)/C=C/C=C/C=C/1C]

40-epi-(N1-tetrazolyl)-rapamycin (ABT-578) has the following structural formula:

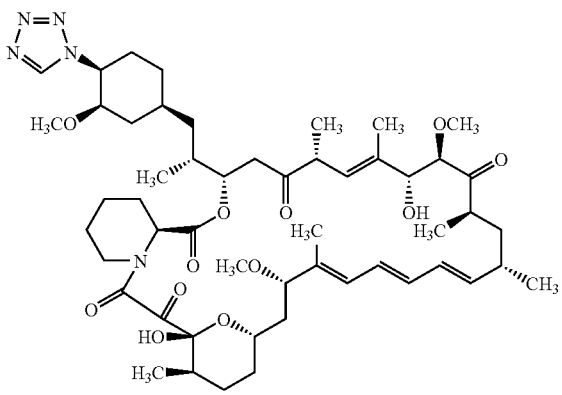 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@H](n3cnnn3)[C@H](OC)C2)CC(=O)[C@H](C)/C=C(\C)[C@@H](O)[C@@H](OC)C(=O)[C@H](C)C[C@H](C)/C=C/C=C/C=C/1C]

Paclitaxel has the following structural formula:

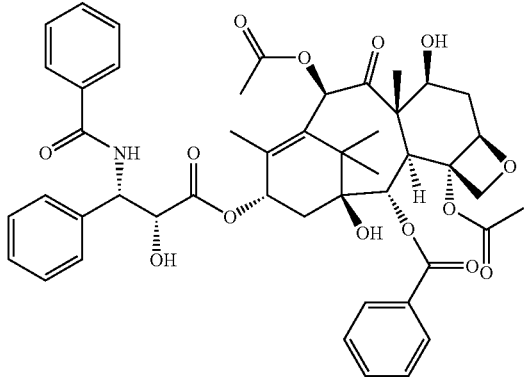 [SMILES: CC(=O)O[C@H]1C(=O)[C@@]2(C)[C@H]([C@H](OC(=O)c3ccccc3)[C@]3(O)C[C@H](OC(=O)[C@H](O)[C@@H](NC(=O)c4ccccc4)c4ccccc4)C(C)=C1C3(C)C)[C@]1(OC(C)=O)CO[C@@H]1C[C@@H]2O]

Docetaxel has the following structural formula:

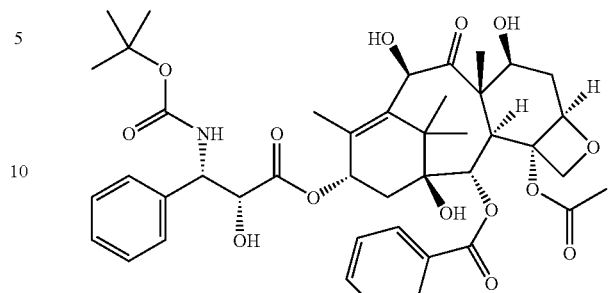

Estradiol has the following structural formula:

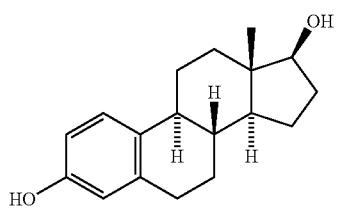

Dexamethasone has the following structural formula:

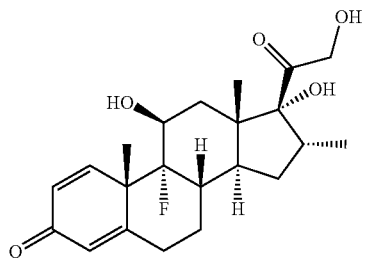

Clobetasol has the following structural formula:

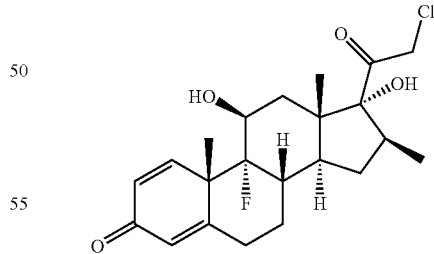

Each of the above mentioned drugs has one or more free hydroxyl groups which can form ester with a carboxyl group in heparin. Specifically, an ester can be formed between a carboxyl group of heparin and the C-31 hydroxyl group of Rapamycin and Rapamycin derivatives.

Alternatively, the prodrug can be made via a hydroxyl group in the heparin molecule and a carboxylic acid, as shown in Scheme 2.

Scheme 2

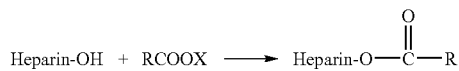

In Scheme 2, R represents a drug molecule or a derivative thereof. Heparin represents a heparin molecule or a moiety or derivative thereof. X represents a leaving group attached to the carboxyl group of the drug molecule. For example, X can be H, a halo group, a carboxylate, mesylate or tosyl group, or any other group capable of leaving the drug molecule in forming the drug/heparin ester bond.

The prodrug can be an ester formed between a hydroxyl group of heparin and a carboxyl group of the drug. The drug can be Aspirin which has structural formula:

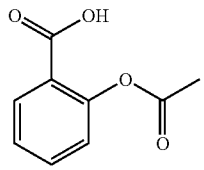

In some other embodiments, the prodrug described herein can be formed via an imine Schiff base by Heparin-CHO with an amine-containing drug (Scheme 3) or vice versa (Scheme 4). As shown in Scheme 3, the aldehyde group of Heparin-CHO can react with the amine group of an amine-containing drug to form an imine Schiff base, which is hydrolytically unstable and can release the amine-containing drug under in vivo conditions. Scheme 4 shows an alternative strategy for forming the prodrug by the reaction of the amino group of Heparin-NH$_2$ with a keto group on the drug molecule to form an imine Schiff base linkage.

Scheme 3

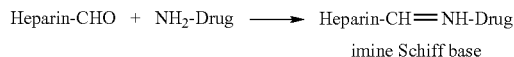

Scheme 4

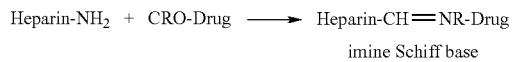

R can be H or an organic moeity that is part of the drug molecule

In still some other embodiments, the prodrug described herein can be formed via an acetal or hemi-acetal by heparin-CHO with a hydroxyl group or hydroxyl groups on a drug (Scheme 5) or vice versa (Scheme 6). The acetal or hemi-acetal can undergo hydrolysis under in vivo conditions to release the drug. As shown in Scheme 5, the aldehyde group of heparin-CHO can react with the hydroxyl group or groups on a drug to form a prodrug with an acetal linkage or hemi-acetal linkage (Scheme 5). Alternatively, the hydroxyl group or groups can react with an aldehyde or keto group on a drug to form a prodrug with an acetal linkage or hemi-acetal linkage (Scheme 6).

Scheme 5

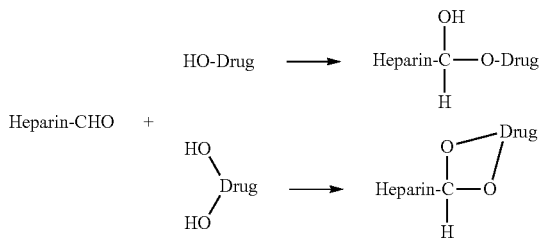

Scheme 6

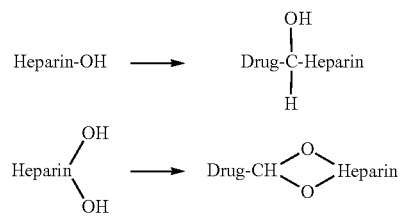

In one embodiment, the hydroxyl group on the C40 position of everolimus can react with the carboxyl group on heparin to form an ester bond so as to form an everolimus/heparin prodrug.

In another embodiment, a drug can form a prodrug with heparin attached to a polymer such as poly(L-lysine-g-ethylene glycol) (PLL-PEG), which can be PLL-g-PEG or PLL-co-PEG. In this embodiment, the amino group in the PLL-PEG can react with a carboxyl group in heparin to form an amide bond via EDC activation and/or NHS activation, as described above. Alternatively, the amino group in the PLL-PEG can react with heparin-CHO to form a Schiff base. A drug such as paclitaxel, docetaxel, or everolimus can then be attached or linked to the heparin via one of the functionalities, such as an amino group, an aldehyde group, a carboxyl group or a hydroxyl group to form a prodrug as per the above description. In addition to heparin, the point of attachment for the drug can also be the PLL backbone via NH$_2$ groups on PLL or PEG via a terminal hydroxyl group, an amino group or an aldehyde group of PEG. Using the same strategy, in some other embodiments, prodrugs can be formed by a drug and a polymer such as poly(L-lysine-hyaluronic acid) (PLL-HA), poly(L-lysine-phosphoryl choline) (PLL-PC), poly(L-lysine-vinylpyrrolidone) (PLL-PVP), poly(ethylimine-ethylene glycol) (PEI-PEG), poly(ethylimine-hyaluronic acid) (PEI-HA), poly(ethylimine-phosphoryl choline) (PEI-PC), and poly(ethylimine-vinylpyrrolidone) (PEI-PVP). These PLL or PEI based copolymers can be graft or block copolymers, e.g., PLL-g-PEG, PLL-g-HA, PLL-g-PC, PLL-g-PVP, PEI-g-PEG, PEI-g-HA, PEI-g-PC, PEI-g-PVP, PLL-co-HA, PLL-co-PC, PLL-co-PVP, PEI-co-PEG, PEI-co-HA, PEI-co-PC, and PEI-co-PVP. Note, in still some other embodiments, the primary amine —NH$_2$ groups in PLL or PEI can be converted to NH$_3^+$ ions on the polymer under an acidic pH to bind or link with heparin.

Coatings Having a Prodrug

The prodrug can be used to form a coating on an implantable device. The prodrug can also be attached to a polymer via the heparin molecule to form a polymer bearing the prodrug defined herein, which can then be coated onto an implantable device. Alternatively, the prodrug can be attached or grafted onto a polymeric coating on an implantable device.

The prodrug provided herein can be used alone to form a coating on a medical device. The prodrug can also be used in combination with a polymeric material. The prodrug can be blended with a polymeric coating material or deposited as a coating on top of a polymeric coating which itself may optionally include a drug. The polymeric material can be any biocompatible polymer such as a hydrophobic polymer, a hydrophilic polymer, a non-fouling polymer, or a combination thereof. The polymeric material can be biodegradable, bioerodable, bioabsorable or biodurable.

In one embodiment, the coating material is a hydrophobic polymer. Representative hydrophobic polymers include, but are not limited to, polystyrene-polyisobutylene-polystyrene block copolymer (SIS), polystyrene, polyisobutylene, polycaprolactone (PCL), poly(L-lactide), poly(D,L-lactide), poly (lactides), polylactic acid (PLA), poly(lactide-co-glycolide), poly(glycolide), polyalkylene, polyfluoroalkylene, polyhydroxyalkanoate, poly(3-hydroxybutyrate), poly(4-hydroxybutyrate), poly(3-hydroxyvalerate), poly(3-hydroxybutyrate-co-3-hydroxyvalerate), poly(3-hydroxyhexanoate), poly(4-hyroxyhexanoate), mid-chain polyhydroxyalkanoate, poly (trimethylene carbonate), poly(ortho ester), polyphosphazenes, poly(phosphoester), poly(tyrosine derived arylates), poly(tyrosine derived carbonates), polydimethyloxanone (PDMS), polyvinylidene fluoride (PVDF), polyhexafluoropropylene (HFP), polydimethylsiloxane, poly (vinylidene fluoride-co-hexafluoropropylene) (PVDF-HFP), poly(vinylidene fluoride-co-chlorotrifluoroethylene) (PVDF-CTFE), poly(butyl methacrylate), poly(methyl methacrylate), poly(methacrylates), poly(vinyl acetate), poly(ethylene-co-vinyl acetate), poly(ethylene-co-vinyl alcohol), poly(ester urethanes), poly(ether-urethanes), poly(carbonate-urethanes), poly(silicone-urethanes), poly(2-hydroxyethyl methacrylate), poly(urea-urethanes) and a combination thereof.

In one embodiment, the coating material is a hydrophilic polymer, such as those previously described. In some embodiments, hydrophilic polymers include, but are not limited to, polymers and co-polymers of PEG acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), hydroxyl bearing monomers such as HEMA, hydroxypropyl methacrylate (HPMA), hydroxypropylmethacrylamide, and 3-trimethylsilylpropyl methacrylate (TMSPMA), poly(ethylene glycol) (PEG), poly(propylene glycol), SIS-PEG, polystyrene-PEG, polyisobutylene-PEG, PCL-PEG, PLA-PEG, PMMA-PEG, PDMS-PEG, PVDF-PEG, PLURONIC™ surfactants (polypropylene oxide-co-polyethylene glycol), poly(tetramethylene glycol), hydroxy functional poly(vinyl pyrrolidone), polyalkylene oxide, dextran, dextrin, sodium hyaluronate, hyaluronic acid, elastin, chitosan, acrylic sulfate, acrylic sulfonate, acrylic sulfamate, methacrylic sulfate, methacrylic sulfonate, methacrylic sulfamate or combination thereof.

In another embodiment, the coating material is a non-fouling polymer such as, for example, poly(ethylene glycol), poly(alkylene oxide), hydroxyethylmethacrylate (HEMA) polymer and copolymers, poly(n-propylmethacrylamide), sulfonated polystyrene, hyaluronic acid (HA), poly(vinyl alcohol), poly(N-vinyl-2-pyrrolidone), sulfonated dextran, phospholipids such as phosphoryl choline (PC) and choline, or combinations thereof.

Examples of Implantable Device

As used herein, an implantable device may be any suitable medical substrate that can be implanted in a human or veterinary patient. Examples of such implantable devices include self-expandable stents, balloon-expandable stents, stent-grafts, grafts (e.g., aortic grafts), artificial heart valves, cerebrospinal fluid shunts, pacemaker electrodes, and endocardial leads (e.g., FINELINE and ENDOTAK, available from Guidant Corporation, Santa Clara, Calif.). The underlying structure of the device can be of virtually any design. The device can be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention.

Method of Use

In accordance with embodiments of the invention, a coating of the various described embodiments can be formed on an implantable device or prosthesis, e.g., a stent. For coatings including one or more active agents, the agent will retain on the medical device such as a stent during delivery and expansion of the device, and be released at a desired rate and for a predetermined duration of time at the site of implantation. Preferably, the medical device is a stent. A stent having the above-described coating is useful for a variety of medical procedures, including, by way of example, treatment of obstructions caused by tumors in bile ducts, esophagus, trachea/bronchi and other biological passageways. A stent having the above-described coating is particularly useful for treating occluded regions of blood vessels caused by abnormal or inappropriate migration and proliferation of smooth muscle cells, thrombosis, and restenosis. Stents may be placed in a wide array of blood vessels, both arteries and veins. Representative examples of sites include the iliac, renal, and coronary arteries.

For implantation of a stent, an angiogram is first performed to determine the appropriate positioning for stent therapy. An angiogram is typically accomplished by injecting a radio-paque contrasting agent through a catheter inserted into an artery or vein as an x-ray is taken. A guidewire is then advanced through the lesion or proposed site of treatment. Over the guidewire is passed a delivery catheter which allows a stent in its collapsed configuration to be inserted into the passageway. The delivery catheter is inserted either percutaneously or by surgery into the femoral artery, brachial artery, femoral vein, or brachial vein, and advanced into the appropriate blood vessel by steering the catheter through the vascular system under fluoroscopic guidance. A stent having the above-described coating may then be expanded at the desired area of treatment. A post-insertion angiogram may also be utilized to confirm appropriate positioning.

While particular embodiments of the present invention have been shown and described, it will be obvious to those skilled in the art that changes and modifications can be made without departing from this invention in its broader aspects.

Therefore, the appended claims are to encompass within their scope all such changes and modifications as fall within the true spirit and scope of this invention.

What is claimed is:

1. A prodrug of a drug, said prodrug comprising the drug, heparin, and a polymer,
   wherein the heparin is covalently linked to the polymer,
   wherein the drug is covalently linked to the heparin,
   wherein the drug is not pharmacologically active in the presence of the covalent linkage between the drug and the heparin,
   wherein the covalent linkage of the drug to the heparin is either hydrolytically or enzymatically unstable,
   wherein the covalent linkage between the drug and the heparin is hydrolytically or enzymatically cleaved under in vivo conditions, and
   wherein the polymer is selected from the group consisting of poly(L-lysine-co-hyaluronic acid) (PLL-co-HA), poly(L-lysine-co-phosphoryl choline) (PLL-co-PC), poly(ethylimine-co-hyaluronic acid) (PEI-co-HA), poly(ethylimine-co-phosphoryl choline) (PEI-co-PC), poly(L-lysine-g-hyaluronic acid) (PLL-g-HA), poly(L-lysine-g-phosphoryl choline) (PLL-g-PC), poly(ethylimine-g-hyaluronic acid) (PEI-g-HA), and poly(ethylimine-g-phosphoryl choline) (PEI-g-PC).

2. The prodrug of claim 1, wherein the prodrug is an ester formed between a carboxyl group of the heparin and a hydroxyl group of the drug or between a carboxyl group of the drug and a hydroxyl group of heparin, wherein the drug is selected from the group consisting of paclitaxel, docetaxel, estradiol, tacrolimus, dexamethasone, rapamycin, 40-O-(2-hydroxy)ethyl-rapamycin (everolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (ABT-578), clobetasol, aspirin, and a combination thereof.

3. The prodrug of claim 1, wherein the heparin is pentasaccharide.

4. A medical device comprising as a coating the prodrug of claim 1.

5. A medical device comprising as a coating the prodrug of claim 2.

6. The prodrug of claim 1, wherein the heparin is a heparin modified with a hydrophobic counter-ion.

7. A medical device comprising as a coating the prodrug of claim 3.

8. The medical device of claim 4, further comprising a polymer selected from the group consisting of a hydrophilic polymer, a hydrophobic polymer, a non-fouling polymer, and combinations thereof.

9. A method of treating a disorder in a human being by implanting in the human being the medical device as defined in claim 4,
   wherein the disorder is selected from the group consisting of atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, and combinations thereof.

* * * * *